(12) United States Patent
Peglion et al.

(10) Patent No.: US 8,415,468 B2
(45) Date of Patent: Apr. 9, 2013

(54) PROCESS FOR THE SYNTHESIS OF IVABRADINE AND ADDITION SALTS THEREOF WITH A PHARMACEUTICALLY ACCEPTABLE ACID

(75) Inventors: Jean-Louis Peglion, Le Vesinet (FR); Aimee Dessinges, Rueil Malmaison (FR); Bernard Serkiz, Servon Brie Comte Robert (FR); Jean-Michel Lerestif, Yvetot (FR); Jean-Pierre Lecouve, Le Havre (FR)

(73) Assignee: Les Laboratoires Servier, Suresnes Cedex (FR)

( * ) Notice: Subject to any disclaimer, the term of this patent is extended or adjusted under 35 U.S.C. 154(b) by 0 days.

(21) Appl. No.: 13/138,333

(22) PCT Filed: Feb. 3, 2010

(86) PCT No.: PCT/FR2010/000080
§ 371 (c)(1),
(2), (4) Date: Aug. 2, 2011

(87) PCT Pub. No.: WO2010/089475
PCT Pub. Date: Aug. 12, 2010

(65) Prior Publication Data
US 2011/0294999 A1    Dec. 1, 2011

(30) Foreign Application Priority Data

Feb. 4, 2009 (FR) ..................... 09 00457

(51) Int. Cl.
*C07D 223/16* (2006.01)
*C07C 303/00* (2006.01)
*C07C 22/00* (2006.01)

(52) U.S. Cl. ............. 540/523; 558/44; 570/183
(58) Field of Classification Search ........... 540/523; 558/44; 570/183
See application file for complete search history.

(56) References Cited

U.S. PATENT DOCUMENTS
5,296,482 A     3/1994   Peglion et al.
2005/0228177 A1  10/2005  Lerestif et al.

FOREIGN PATENT DOCUMENTS
EP    0534859       3/1993
WO    WO 2008/065681  6/2008
WO    WO 2008/125006  10/2008

OTHER PUBLICATIONS
International Search Report for PCT/FR2010/000080 of Jun. 8, 2010.

*Primary Examiner* — Bruck Kifle
(74) *Attorney, Agent, or Firm* — Hueschen and Sage

(57) ABSTRACT

Process for the synthesis of ivabradine of formula (I):

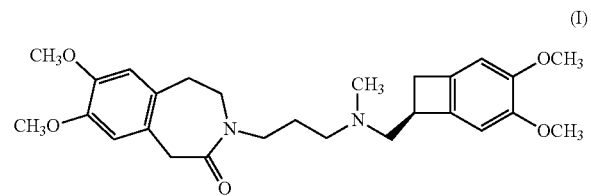

(I)

and addition salts thereof with a pharmaceutically acceptable acid.

12 Claims, No Drawings

PROCESS FOR THE SYNTHESIS OF IVABRADINE AND ADDITION SALTS THEREOF WITH A PHARMACEUTICALLY ACCEPTABLE ACID

The present invention relates to a process for the synthesis of ivabradine of formula (I):

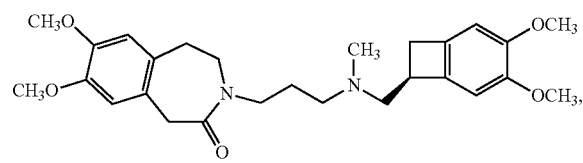

(I)

or 3-{3-[{[(7S)-3,4-dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one,
addition salts thereof with a pharmaceutically acceptable acid and hydrates thereof.

Ivabradine, and its addition salts with a pharmaceutically acceptable acid, and more especially its hydrochloride, have very valuable pharmacological and therapeutic properties, especially bradycardic properties, making those compounds useful in the treatment or prevention of various clinical situations of myocardial ischaemia such as angina pectoris, myocardial infarct and associated rhythm disturbances, and also in various pathologies involving rhythm disturbances, especially supraventricular rhythm disturbances, and in heart failure.

The preparation and therapeutic use of ivabradine and addition salts thereof with a pharmaceutically acceptable acid, and more especially its hydrochloride, have been described in the European patent specification EP 0 534 859.

That patent specification describes the synthesis of ivabradine hydrochloride starting from the compound of formula (II):

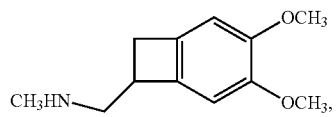

(II)

which is resolved to yield the compound of formula (III):

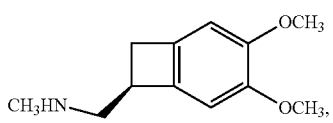

(III)

which is reacted with the compound of formula (IV):

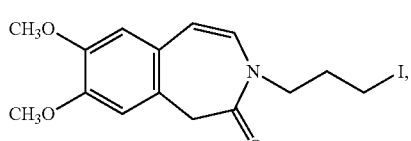

(IV)

to yield the compound of formula (V):

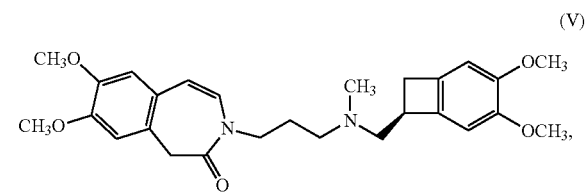

(V)

the catalytic hydrogenation of which yields ivabradine, which is then converted into its hydrochloride.

The disadvantage of that synthesis route is that it results in ivabradine in a yield of only 1%.

In view of the pharmaceutical value of this compound, it has been important to be able to obtain it by an effective synthesis process resulting in ivabradine in a good yield.

The present invention relates to a process for the synthesis of the compound of formula (VI), in its racemic or optically active form:

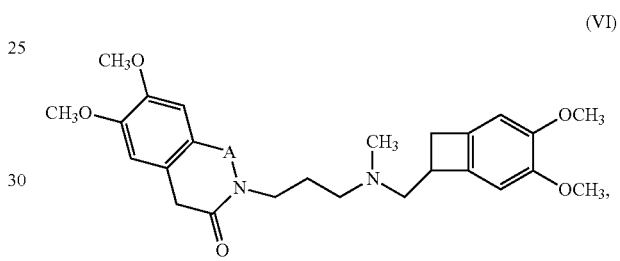

(VI)

wherein A represents $H_2C-CH_2$ or $HC=CH$,
characterised in that the compound of formula (VII), in racemic or optically active form:

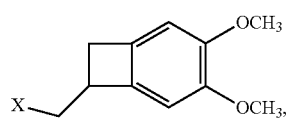

(VII)

wherein X represents a halogen atom, a mesylate group or a tosylate group,
is subjected to an alkylation reaction with the compound of formula (VIII):

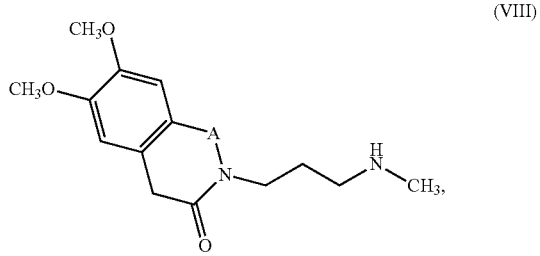

(VIII)

wherein A is as defined hereinbefore,
in the presence of a base,
in an organic solvent.

In a preferred embodiment of the invention, the compound of formula (VII) is in optically active form, and more especially of configuration (S).

In the case where A represents H₂C—CH₂, the product of alkylation of the compound of formula (VII) of configuration (S) with the compound of formula (VIII) is ivabradine of formula (I):

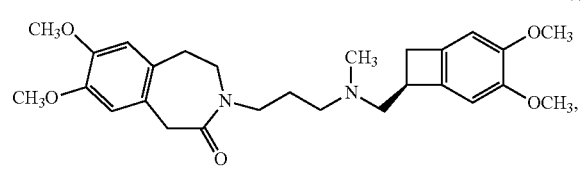
(I)

which may optionally be converted into addition salts thereof with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into hydrates thereof.

In the case where A represents HC=CH, the product of alkylation of the compound of formula (VII) of configuration (S) with the compound of formula (VIII) is the compound of formula (V):

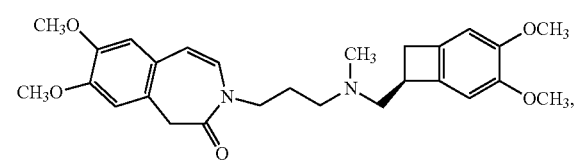
(V)

the catalytic hydrogenation of which yields ivabradine of formula (I):

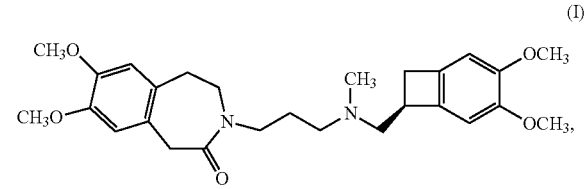
(I)

which may optionally be converted into addition salts thereof with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into hydrates thereof.

In another preferred embodiment of the invention, the compound of formula (VII) is in racemic form. The alkylation reaction of the racemic compound of formula (VII) with the compound of formula (VIII) is then followed by a step of optical resolution of the compound of formula (VI) obtained.

In the case where A represents H₂C—CH₂, the product obtained after the step of optical resolution of the compound of formula (VI) is ivabradine of formula (I):

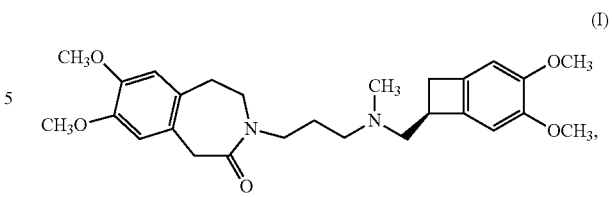
(I)

which may optionally be converted into addition salts thereof with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into hydrates thereof.

In the case where A represents HC=CH, the product obtained after the step of optical resolution of the compound of formula (VI) is the compound of formula (V):

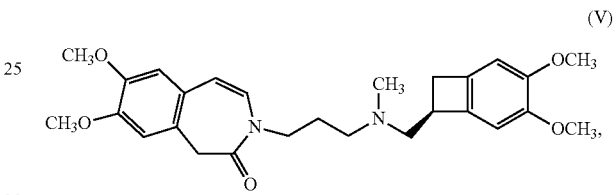
(V)

the catalytic hydrogenation of which yields ivabradine of formula (I):

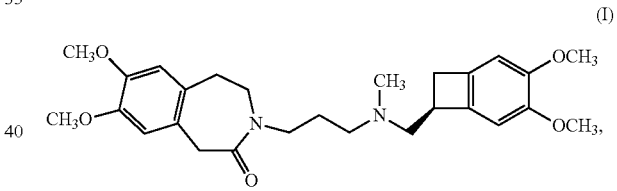
(I)

which may optionally be converted into addition salts thereof with a pharmaceutically acceptable acid selected from hydrochloric acid, hydrobromic acid; sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into hydrates thereof.

Among the bases which may be used to carry out the alkylation reaction of the compound of formula (VII) with the compound of formula (VIII) there may be mentioned, without implying any limitation, potassium carbonate, sodium carbonate, caesium carbonate, potassium hydrogen carbonate and sodium hydrogen carbonate.

Preference is given to the base used to carry out the alkylation reaction of the compound of formula (VII) with the compound of formula (VIII) being potassium carbonate.

Among the solvents which may be used to carry out the alkylation reaction of the compound of formula (VII) with the compound of formula (VIII) there may be mentioned, without implying any limitation, acetonitrile, acetone or butan-2-one.

Preference is given to the solvent used to carry out the alkylation reaction of the compound of formula (VII) with the compound of formula (VIII) being acetonitrile.

The compounds of formula (VIIa), in their racemic or optically active forms, which are particular cases of the compounds of formula (VII) wherein X represents a halogen atom or a mesylate group, are new products which are useful as synthesis intermediates in the chemical or pharmaceutical industry, especially in the synthesis of ivabradine, addition salts thereof with a pharmaceutically acceptable acid and hydrates thereof, and as such they form an integral part of the present invention.

The Examples hereinbelow illustrate the invention.

List of abbreviations used:
DMF: N,N-dimethylformamide
IR: infrared

The melting points (m.p.) were measured on a Kofler block.

EXAMPLE 1

7,8-Dimethoxy-3-[3-(methylamino)propyl]-1,3,4,5-tetrahydro-2H-3-benzazepin-2-one Dissolve 50 g (0.18 mol) of 3-(7,8-dimethoxy-2-oxo-1,2,4,5-tetrahydro-benzo[d]azepin-3-yl)-propionaldehyde in 625 mL of methanol. Cool the resulting solution to 0° C. Then add 62.5 mL (0.81 mol; 4.5 equivalents) of 40% aqueous methylamine solution. Stir for one hour at 0° C., and then add 7.5 g (0.2 mol; 1.1 equivalents) of $NaBH_4$. Stir for 30 minutes at 0° C. and then stir for 12 hours at ambient temperature. Evaporate off the methanol. The residue is taken up in aqueous hydrochloric acid solution (1N), washed with ethyl acetate and then the aqueous phase is brought to pH=8 by adding 20% sodium hydroxide solution and extracted with dichloromethane. The organic, phase is washed with water, dried over $MgSO_4$, filtered and then evaporated to dryness to obtain 52 g of an oil.

The resulting oil is purified by flash chromatography over 1.5 kg of silica (eluant: dichloromethane/ethanol/$NH_4OH$: 80/20/2). 42 g of expected product are obtained in the form of a white solid.

Yield=80%
m.p.=68-70° C.

EXAMPLE 2

7,8-Dimethoxy-3-[3-(methylamino)propyl]-1,3-dihydro-2H-3-benzazepin-2-one

Step 1 tert-Butyl [3-(7,8-dimethoxy-2-oxo-1,2-dihydro-3H-3-benzazepin-3-yl)propyl]methyl carbamate Suspend 1.7 g (7.8 mmol) of 7,8-dimethoxy-1,3-dihydro-2H-3-benzazepin-2-one in 35 mL of DMF and then add 374 mg (9.35 mmol, 1.2 equivalents) of sodium hydride (60% suspension in oil). A clear pale-yellow solution is obtained which is stirred for one hour at 25° C. Then, 1.94 g (9.35 mmol, 1.2 equivalents) of tert-butyl (3-chloropropyl)methylcarbamate dissolved in 10 mL of DMF are added dropwise. Heating is carried out at 50° C. overnight and then the solvent is evaporated off to dryness. The residue is taken up in water and extracted with dichloromethane. The organic phase is dried over $MgSO_4$, filtered and then evaporated to dryness. There are obtained 4.2 g of an oil which is purified by flash chromatography over 200 g of silica (eluant: dichloromethane/ethyl acetate: 80/20). There are then obtained 2.3 g of the title product in the form of a colourless oil.

Yield=77%
IR (pure): υ=1685, 1659, 1155, 1102, 872, 770 $cm^{-1}$.

Step 2

7,8-Dimethoxy-3-[3-(methylamino)propyl]-1,3-dihydro-2H-3-benzazepin-2-one

Dissolve 1.9 g (4.86 mmol) of the product obtained in Step 1 in 30 mL of ethanol, and to the resulting solution add 7 mL (24.3 mmol, 5 equivalents) of ethanolic HCl (3.5N). Heat overnight at 60° C. and evaporate the reaction mixture to dryness. The residue obtained is taken up in water, and the aqueous phase is then brought to pH=8 by adding 20% sodium hydroxide solution and extracted with dichloromethane. The organic phase is washed with water, dried over $MgSO_4$, filtered and then evaporated to dryness. 1.1 g of the title product are obtained in the form of a colourless oil.

Yield=78%
IR (pure): υ=3400, 1651, 1610, 1510, 856, 710 $cm^{-1}$.

EXAMPLE 3

(R,S)-7-(iodomethyl)-3,4-dimethoxybicyclo[4.2.0]octa-1,3,5-triene

To 60 mL of dichloromethane add, in order: 4.8 g of $P(Ph)_3$ (18.5 mmol; 1.2 equivalents), 1.2 g of imidazole (18.5 mmol; 1.2 equivalents), wait until a clear solution is obtained and then add 4.7 g of iodine (18.5 mmol; 1.2 equivalents). The formation of a fine precipitate of imidazole iodohydrate is observed. Then to the resulting mixture add, dropwise, 3 g (15.4 mmol) of (3,4-dimethoxybicyclo[4.2.0]octa-1,3,5-trien-7-yl)methanol dissolved in 15 mL of dichloromethane; an exothermic temperature rise from 20° C. to 28° C. is observed. Stir for 12 hours at ambient temperature.

Insoluble material is filtered off; then evaporation to dryness is carried out to obtain 15 g of a residue in the form of an oil.

The resulting product is purified by flash chromatography over 500 g of silica (eluant=dichloromethane/cyclohexane: 80/20). There are obtained 4 g of iodinated compound in the form of a green oil which crystallises at ambient temperature.

Yield=85%
m.p.=55-60° C.

EXAMPLE 4

(R,S)-(3,4-dimethoxybicyclo[4.2.0]octa-1,3,5-trien-7-yl)methyl methanesulphonate Dissolve 4 g (20.6 mmol) of (3,4-dimethoxybicyclo[4.2.0]octa-1,3,5-trien-7-yl)methanol in 50 mL of dichloromethane. Cooling to 0° C. is carried out and 4.3 mL (31.0 mmol, 1.5 equivalents) of triethylamine are added. 1.9 mL of mesyl chloride (24.7 mmol, 1.2 equivalents) dissolved in 10 mL of dichloromethane are then added dropwise. Stirring overnight at ambient temperature is carried out. The organic phase is washed with aqueous HCl solution (1N) and then with water, and is dried over $MgSO_4$, filtered and evaporated to dryness to obtain 4.7 g of the title product in the form of a beige solid.

Yield=84%
m.p.=98-100° C.

EXAMPLE 5

(R,S)-3-(3-{[(3,4-dimethoxybicyclo[4.2.0]octa-1,3,
5-trien-7-yl)methyl]-(methyl)amino}propyl)-7,8-
dimethoxy-1,3,4,5-tetrahydro-2H-3-benzazepin-2-
one 1 g (3.28 mmol) of 7-(iodomethyl)-3,4-dimethoxybicyclo [4.2.0]octa-1,3,5-triene is dissolved in 20 mL of acetonitrile. There are added 907 mg (2 equivalents) of $K_2CO_3$ and 959 mg (3.28 mmol) of 7,8-dimethoxy-3-[3-(methylamino)propyl]-1,3,4,5-tetrahydro-2H-3-benzazepin-2-one. The resulting reaction mixture is heated at reflux for 4 hours. Cooling is carried out, insoluble material is filtered off and then evaporation to dryness is carried out to obtain 2 g of an oil which is purified by flash chromatography over 100 g of silica (eluant=dichloromethane/ethanol/$NH_4OH$: 90/10/1). There are obtained 780 mg of expected product in the form of a colourless oil which crystallises at ambient temperature.

Yield=51%
m.p.=98-100° C.

Alternative Method 1 g (3.67 mmol) of (R,S)-(3,4-dimethoxybicyclo[4.2.0] octa-1,3,5-trien-7-yl)methyl methane-sulphonate obtained in Example 4 is dissolved in 20 mL of acetonitrile. There are added 1 g (7.34 mmol, 2 equivalents) of $K_2CO_3$ and 1.07 g (3.67 mmol) of 7,8-dimethoxy-3-(3-methyl-amino-propyl-1, 3,4,5-tetrahydro-benzo[d]azepin-2-one. The resulting reaction mixture is heated at reflux for 48 hours. Cooling is carried out, insoluble material is filtered off and then evaporation to dryness is carried out to obtain 1.8 g of an oil which is purified by flash chromatography first over 100 g of silica (eluant=dichloromethane/ethanol/$NH_4OH$: 90/10/1) and then over 100 g of silica (eluant=dichloromethane/ethanol/ $NH_4OH$: 95/5/0.5) to obtain the title product.

EXAMPLE 6

3-{3-[{[(7S)-3,4-dimethoxybicyclo[4.2.0]octa-1,3,5-
trien-7-yl]methyl}-(methyl)amino]propyl}-7,8-
dimethoxy-1,3,4,5-tetrahydro-2H-3-benzazepin-2-
one hydrochloride (optical resolution)

2.1 g of the racemic compound obtained in Example 5 are separated on a 60 cm×60 mm column packed with 2.1 kg of Chiralpak® AD phase (particle size: 20 μm). The eluant used is a mixture of ethanol/acetonitrile/diethylamine (10/90/0.1 by volume) at a flow rate of 50 mL/min. The associated ultraviolet detector is used at a wavelength of 280 nm.

There is obtained 0.95 g of the enantiomer of configuration (R) in the form of a white meringue and then 0.95 g of the enantiomer of configuration (S) also in the form of a white meringue.

The hydrochloride of the enantiomer of configuration (S) is then obtained by following the procedure described in patent specification EP 0 534 859 (Example 2, Step E).

EXAMPLE 7

3-{3-[[(3,4-dimethoxybicyclo[4.2.0]octa-1,3,5-trien-
7-yl)methyl](methyl)amino]propyl}-7,8-dimethoxy-
1,3-dihydro-2H-3-benzazepin-2-one 1 g (3.28 mmol) of 7-(iodomethyl)-3,4-dimethoxy[4.2.0] octa-1,3,5-triene is dissolved in 20 mL of acetonitrile. There are added 907 mg (2 equivalents) of $K_2CO_3$ and 952 mg (3.28 mmol) of 7,8-dimethoxy-3-[3-(methylamino)propyl]-1,3-dihydro-2H-3-benzazepin-2-one. The reaction mixture is heated at reflux for 4 hours. Cooling is carried out, insoluble material is filtered off and then evaporation to dryness is carried out to obtain 2 g of an oil which is purified by flash chromatography over 100 g of silica (eluant: dichloromethane/ethanol/$NH_4OH$: 90/10/1). There are obtained 700 mg of the title product in the form of an oil.

Yield=47%

IR (pure): υ=1656, 1607, 1511, 1273, 1206, 1101, 836, 760 cm$^{-1}$.

Alternative Method 1 g (3.67 mmol) of (3,4-dimethoxy[4.2.0]octa-1,3,5-trien-7-yl)methyl methanesulphonate is dissolved in 20 mL of acetonitrile. There are added 1 g (7.34 mmol, 2 equivalents) of $K_2CO_3$ and 1.06 g (3.67 mmol) of (7,8-dimethoxy-3-[3-(methylamino)propyl]-1,3-dihydro-2H-3-benzazepin-2-one. The reaction mixture is heated at reflux for 12 hours. Cooling is carried out, insoluble material is filtered off and then evaporation to dryness is carried out to obtain 1.9 g of an oil which is purified by flash chromatography first over 100 g of silica (eluant: dichloromethane/ethanol/$NH_4OH$: 90/10/1) and then over 100 g of silica (eluant: dichloromethane/ethanol/ $NH_4OH$: 95/5/0.5) to obtain the title product.

EXAMPLE 8

3-{3-[{[(7S)-3,4-dimethoxybicyclo[4.2.0]octa-1,3,5-
trien-7-yl]methyl}-(methyl)amino]propyl}-7,8-
dimethoxy-1,3,4,5-tetrahydro-2H-3-benzazepin-2-
one hydrochloride 1.4 g of the racemic compound obtained in Example 7 are separated on a 60 cm×60 mm column packed with 3 kg of Chiralpak® T101 phase (particle size: 20 μm). The eluant used is a mixture of ethanol/acetonitrile/diethylamine (10/90/ 0.1 by volume) at a flow rate of 100 mL/min. The associated ultraviolet detector is used at a wavelength of 280 nm. 0.56 g of the enantiomer of configuration (R) is obtained in the form of a colourless oil and then 0.62 g of the enantiomer of configuration (S) also in the form of a colourless oil.

The compound of configuration (S) is then hydrogenated by following the procedure described in patent specification EP 0 534 859 (Example 1, Step D). The hydrochloride of the compound obtained is prepared by following the procedure described in patent specification EP 0 534 859 (Example 2, Step E).

EXAMPLE 9

3-{3-[{[(7S)-3,4-dimethoxybicyclo[4.2.0]octa-1,3,5-
trien-7-yl]methyl}-(methyl)amino]propyl}-7,8-
dimethoxy-1,3,4,5-tetrahydro-2H-3-benzazepin-2-
one hydrochloride By proceeding as in Example 5, starting from (7S)-(iodomethyl)-3,4-dimethoxybicyclo[4.2.0]octa-1,3,5-triene (or from (7S)-(3,4-dimethoxybicyclo[4.2.0]octa-1,3,5-trien-7-yl)methyl methanesulphonate) and from 7,8-dimethoxy-3-[3-(methylamino)-propyl]-1,3,4,5-tetrahydro-2H-3-benzazepin-2-one, there is obtained ivabradine base, which is then converted into its hydrochloride by following the procedure described in patent specification EP 0 534 859 (Example 2, Step E).

EXAMPLE 10

3-{3-[{[(7S)-3,4-dimethoxybicyclo[4.2.0]octa-1,3,5-trien-7-yl]methyl}-(methyl)amino]propyl}-7,8-dimethoxy-1,3,4,5-tetrahydro-2H-3-benzazepin-2-one hydrochloride By proceeding as in Example 7, starting from (7S)-(iodomethyl)-3,4-dimethoxybicyclo-[4.2.0]octa-1,3,5-triene (or from (7S)-(3,4-dimethoxybicyclo[4.2.0]octa-1,3,5-trien-7-yl)methyl methanesulphonate) and from 7,8-dimethoxy-3-[3-(methylamino)propyl]-1,3-dihydro-2H-3-benzazepin-2-one, there is obtained a compound which is hydrogenated by following the procedure described in patent specification EP 0 534 859 (Example 1, Step D) to yield ivabradine base, which is then converted into its hydrochloride by following the procedure described in patent specification EP 0 534 859 (Example 2, Step E).

The invention claimed is:

1. A process for the synthesis of the compound formula (VI), in its racemic or optically active form:

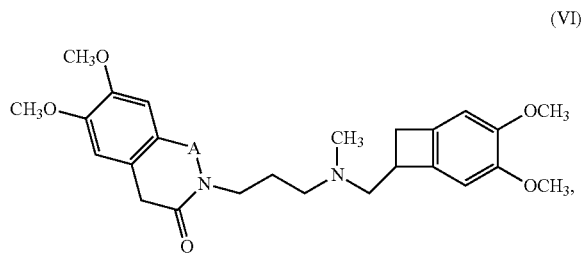

(VI)

wherein A represents $H_2C-CH_2$ or $HC=CH$,
wherein a compound of formula (VII), in racemic or optically active form:

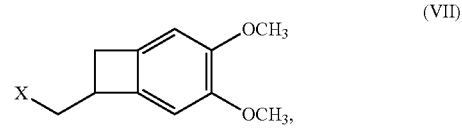

(VII)

wherein X represents a halogen atom, a mesylate group or a tosylate group,
is subjected to an alkylation reaction with a compound of formula (VIII):

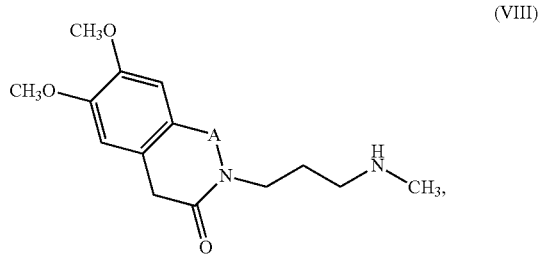

(VIII)

in the presence of a base,
in an organic solvent.

2. A process according to claim 1, wherein the compound of formula (VII) is in optically active form.

3. The process according to claim 2, wherein the compound of formula (VII) is in the (S) configuration.

4. The process according to claim 2, wherein the group A represents $H_2C-CH_2$, and wherein the product of the alkylation reaction of the compound of formula (VII) with the compound of formula (VIII) is ivabradine of formula (I):

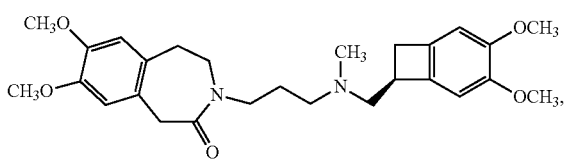

(I)

which may optionally be converted into addition salts thereof with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and/or into hydrates thereof.

5. The process according to claim 2, wherein the group A represents $HC=CH$, and wherein the product of the alkylation reaction of the compound of formula (VII) with the compound of formula (VIII) is the compound of formula (V):

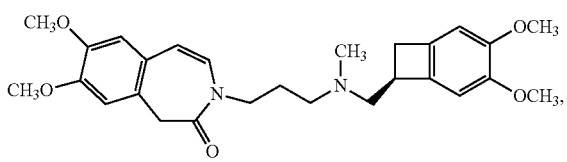

(V)

the catalytic hydrogenation of which yields ivabradine of formula (I):

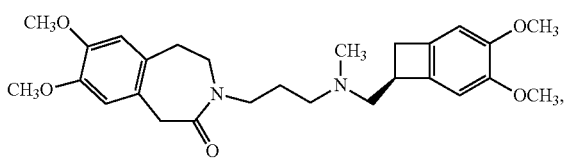

(I)

which may optionally be converted into addition salts thereof with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and/or into hydrates thereof.

6. The process according to claim 1, wherein the compound of formula (VII) is in racemic form, and wherein the alkylation reaction of the compound of formula (VII) with the compound of formula (VIII) is followed by a step of optical resolution of the racemic compound of formula (VI) obtained.

7. The process according to claim 6, wherein A represents $H_2C-CH_2$, and wherein the product obtained after the step of optical resolution of the compound of formula (VI) is ivabradine of formula (I):

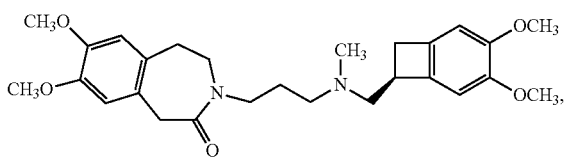

(I)

which may optionally be converted into addition salts thereof with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and/or into hydrates thereof.

8. The process according to claim 6, wherein A represents HC=CH, and wherein the product obtained after the step of optical resolution of the compound of formula (VI) is the compound of formula (V):

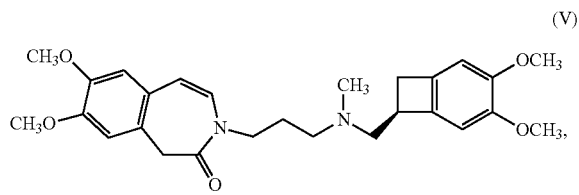
(V)

the catalytic hydrogenation of which yields ivabradine of formula (I):

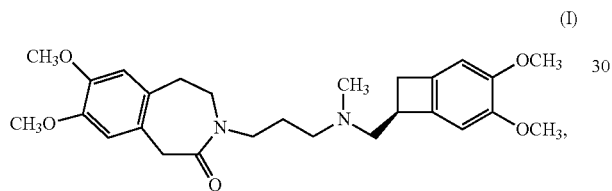
(I)

which may optionally be converted into addition salts thereof with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and/or into hydrates thereof.

9. The process according to claim 1, wherein the base used to carry out the alkylation reaction of the compound of formula (VII) with the compound of formula (VIII) is selected from potassium carbonate, sodium carbonate, caesium carbonate, potassium hydrogen carbonate and sodium hydrogen carbonate.

10. The process according to claim 1, wherein the base used to carry out the alkylation reaction of the compound of formula (VII) with the compound of formula (VIII) is potassium carbonate.

11. The process according to claim 1, wherein the solvent used to carry out the alkylation reaction of the compound of formula (VII) with the compound of formula (VIII) is selected from acetonitrile, acetone and butan-2-one.

12. A compound of formula (VIIa), in its racemic or optically active form:

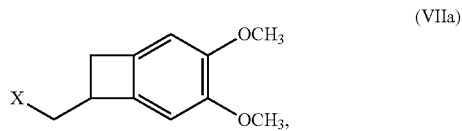
(VIIa)

wherein X represents a halogen atom or a mesylate group.

* * * * *